(12) United States Patent
Kishimoto et al.

(10) Patent No.: US 6,284,499 B1
(45) Date of Patent: Sep. 4, 2001

(54) METHOD FOR PRODUCING L-SORBOSE AND APPARATUS FOR CULTURING MICROORGANISMS

(75) Inventors: Katsumitsu Kishimoto; Kazuhiko Kintaka; Hiroyuki Yoshinaga, all of Hikari (JP)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/101,093

(22) Filed: Aug. 3, 1993

Related U.S. Application Data

(63) Continuation of application No. 07/982,007, filed on Nov. 24, 1992, now abandoned, which is a continuation of application No. 07/662,400, filed on Feb. 27, 1991, now abandoned, which is a continuation of application No. 07/134,078, filed on Dec. 17, 1987, now abandoned.

(30) Foreign Application Priority Data

Dec. 25, 1986 (JP) .................................................. 61-312470

(51) Int. Cl.$^7$ ....................................................... C12P 19/02
(52) U.S. Cl. .......................... 435/105; 435/147; 435/155; 435/252
(58) Field of Search ..................................... 435/105, 147, 435/252, 818, 822, 155

(56) References Cited

U.S. PATENT DOCUMENTS 4,413,058 * 11/1983 Arcuri et al. ........................ 435/161

FOREIGN PATENT DOCUMENTS

| 0092771 | * 11/1983 | (EP) . |
| 175607 | 3/1986 | (EP) . |
| 233050 | 8/1987 | (EP) . |

OTHER PUBLICATIONS

Slave et al., Chemical Abstracts 100:173185a, 1984.
Zolotarev et al., Chemical Abstracts 88:188179z, 1978.
Yamada et al., Chemical Abstracts 91:106578 p, 1979.
Mori et al., J. Chem. Eng. Japan, vol. 14, No. 1, 1981, pp. 65–70.*

* cited by examiner

Primary Examiner—Leon B. Lankford, Jr.
(74) Attorney, Agent, or Firm—Davidson, Davidson & Kappel, LLC

(57) ABSTRACT

A method for producing L-sorbose by microbiological oxidation of D-sorbitol which comprises adding D-sorbitol to a culture liquid in such a concentration that it does not go up to over about 5% during and after the growth phase of a microorganism used, while circulating a culture exhaust gas enriched with oxygen gas, and releasing a part of said exhaust gas out of the system. An apparatus for culturing microorganisms suitable for the method is also disclosed.

12 Claims, 3 Drawing Sheets

METHOD FOR PRODUCING L-SORBOSE AND APPARATUS FOR CULTURING MICROORGANISMS

This application is a continuation of now abandoned application Ser. No. 07/982,007 filed Nov. 24, 1992, which was a continuation application of now abandoned application Ser. No. 07/662,400 filed on Feb. 27, 1991, which was a continuation application of now abandoned Ser. No. 07/134,078 filed Dec. 17, 1987.

FIELD OF THE INVENTION

The present invention relates to a method for producing L-sorbose by using microorganisms and an apparatus for culturing microorganisms suitable for such a method.

BACKGROUND OF THE INVENTION

L-Sorbose is one of the naturally occurring ketohexoses, which is contained in juice of the rowan tree, etc., and it is an important substance as a raw material in vitamin C synthesis. L-Sorbose is produced by fermentation wherein D-sorbitol is oxidized by microorganisms, for example, bacteria of the genus Gluconobacter.

According to a conventional fermentation production of L-sorbose, a yield of conversion of the raw material, D-sorbitol, into L-sorbose is at highest about 93%, and there are formed considerable amounts of by-products such as 5-ketofructose, D-fructose, 2-ketogluconic acid, etc. In order to reduce the raw material cost of vitamin C, it is requested to increase the yield of conversion of D-sorbitol into L-sorbose more than that in a conventional process and to inhibit formation of the above by-products to as little as possible.

In our European Patent Application No. 233050 (A2), there is disclosed that L-sorbose can be produced in a higher yield from D-sorbitol by microbiological oxidation using a microorganism which belongs to the genus Gluconobacter and which is decreased in the ability to grow with D-sorbitol as the single carbon source compared with that of its parent strains.

By the way, when the concentration of D-sorbitol in a culture medium goes up to over about 5% during and after the growth phase of the microorganisms, they are inhibited due to both high concentrations of the substrate (D-sorbitol) and the product (L-sorbose), which results in delay of the rate of oxidation. Accordingly, it is necessary to control the concentration of D-sorbitol below about 5%. However, when the concentration of the substrate is taken as a rate-determining step, there is a problem that the formation of by-products (fructose, 2-ketogluconic acid, etc.) is increased.

In addition, in this type of a production method, sometimes, a culture exhaust gas containing oxygen in a high concentration is recovered by a compressor, and it is circulated and reused in a culture liquid to save resources. In this case, carbon dioxide gas generated by respiration of the microorganisms is accumulated in the exhaust gas and, when the concentration of carbon dioxide gas goes up to over 10%, the growth rate of the microorganisms and the rate of oxidation are strongly inhibited. Accordingly, in a conventional method, there is employed carbon dioxide gas removing means using an adsorbent such as sodium hydroxide, activated charcoal, etc. However, when such means are employed, there are many problems such as increase in the production cost because of necessity of an adsorption column, an adsorbent and the like and further necessity of maintenance thereof.

Japanese Patent Kokoku No. 61-5709 discloses a method and an apparatus for culturing microorganisms such as fungi. In this publication, a gas enriched with oxygen is prepared from air by adsorbing nitrogen therein, and is used to control the partial pressure of carbon dioxide gas in a culture tank as well as to control the concentration of dissolved oxygen in a culture liquid.

OBJECTS OF THE INVENTION

One object of the present invention is to improve a conversion rate of D-sorbitol into L-sorbose in the production of L-sorbose by microbiological oxidation.

Another object of the present invention is to improve a yield of L-sorbose per batch by properly controlling a concentration of D-sorbitol during and after the growth phase to oxidize a high concentration of D-sorbitol into L-sorbose in a short period of time.

Another object of the present invention is to simplify facilities and maintenance thereof in the production of L-sorbose.

Still another object of the present invention is to reduce the production cost of L-sorbose by removing carbon dioxide gas in a culture exhaust gas to be reused without using any adsorbent to control the partial pressure of carbon dioxide gas properly.

These objects as well as other objects and advantages of the present invention will become apparent to those skilled in the art from the following description with reference to the accompanying drawings.

SUMMARY OF THE INVENTION

Figure 1:
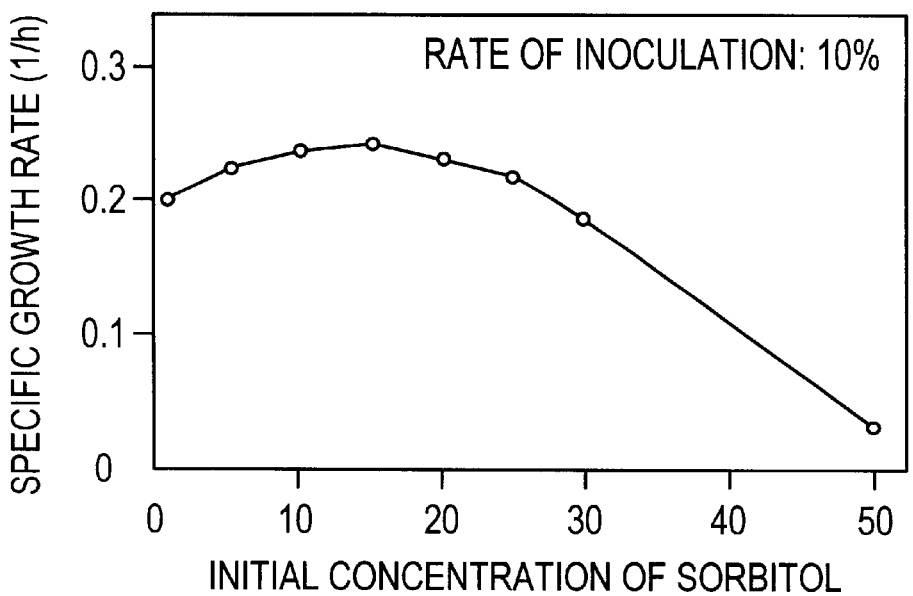
FIG. 1 is a graph illustrating the relationship between an initial charge concentration of D-sorbitol and a specific growth rate.

According to the present invention, there is provided a method for producing L-sorbose by microbiological oxidation of D-sorbitol which comprises the steps of, adding D-sorbitol to a culture liquid in such a concentration that it does not go up to over about 5% in culturing during and after the growth phase of a microorganism used, while circulating a culture exhaust gas which has been enriched with oxygen gas to control a concentration of dissolved oxygen, and releasing a part of said exhaust gas out of the system to control the partial pressure of carbon dioxide gas in the circulating gas.

The present invention also provides an apparatus for culturing microorganisms, particularly, those having L-sorbose producing ability, which comprises, a culture tank for culturing the microorganism equipped with a stirrer, a gas inlet provided at the lower part of the tank and an exhaust vent provided at the upper part of the tank;

a substrate feeding device for adding a culture substrate to said culture tank;

an oxygen supply device comprising a liquid oxygen storage tank and an evaporator for supplying said culture tank with a culture exhaust gas which has been enriched with oxygen gas;

a dissolved oxygen concentration detector for detecting dissolved oxygen in a culture liquid in said culture tank to output a signal of the concentration of dissolved oxygen;

a dissolved oxygen controller for controlling supply of dissolved oxygen by detecting said signal of the concentration of dissolved oxygen;

a carbon dioxide gas measuring device for measuring the partial pressure of carbon dioxide gas in a culture exhaust gas, which is provided to an exhaust gas pipe from said culture tank;

an exhaust gas release device for releasing a part of the culture exhaust gas out of the system by detecting said partial pressure of carbon dioxide gas;

a conduit for circulating the remainder of said culture exhaust gas into the gas inlet of the culture tank; and an air supply device for supplying said culture tank with air.

In the method of the present invention, a yield of L-sorbose can be improved in comparison with a conventional method. That is, a yield of L-sorbose based on D-sorbitol is not more than about 93% in a conventional method, whereas, in the present invention, a yield can be increased to 2 to 3% more than that of the conventional method. Further, the production of by-products such as D-fructose, 2-ketogluconic acid, 5-ketofructose and the like can be minimized. Further, according to the present invention, a high concentration of D-sorbitol can be oxidized to L-sorbose within a short period of time and a yield per batch can be improved because the concentration of D-sorbitol in a culture medium during and after the growth phase is controlled so that it does not go up to over 5%.

Furthermore, in the culture apparatus of the present invention, the exhaust gas is reused to save resources to enhance its economic advantages. Further, the apparatus of the present invention can be simplified and is advantageous in view of maintenance thereof because carbon dioxide gas in the exhaust gas is diluted and a part of the exhaust gas is released out of the system instead of using an adsorbent as in a conventional apparatus.

By the above various advantages, L-sorbose, the cost of which occupies a very high proportion in the raw material cost of vitamin C production, can be supplied economically in comparison with a conventional method and, therefore, the production cost of vitamin C which has wide utility in medicines, food and the like can be reduced.

DETAILED DESCRIPTION OF THE INVENTION

The present invention provides a method for producing L-sorbose by microbiological oxidation of D-sorbitol which comprises the steps of, (1) adding D-sorbitol to a culture liquid in such a concentration that it does not go up to over about 5% in culturing during and after the growth phase of a microorganism used, while (2) circulating and aerating a culture exhaust gas which has been enriched with oxygen gas to increase the partial pressure of oxygen into the culture liquid to control a concentration of dissolved oxygen, and (3) releasing a part of said culture exhaust gas out of the system to control the partial pressure of carbon dioxide gas in the circulating gas.

In the production method of the present invention, any microorganism which has the ability to oxidize D-sorbitol into L-sorbose can be used. Examples of the microorganisms include bacteria of the genus Gluconobacter, for example, seed strains of *Gluconobacter suboxydans* or *Gluconobacter oxydans*. Specific examples of the strains are, for example, *Gluconobacter suboxydans* IFO 3254, IFO 3257, IFO 12528, IFO 3255, IFO 3256, IFO 3258 or IFO 3291 and further, *Gluconobacter oxydans* IFO 3189. These strains are aerobic and gram-negative rod bacteria having motility, grow at acidic pH, and produce acetic acid from ethanol, and are known strains listed on "List of Cultures, 1984, Seventh Edition" published by Institute for Fermentation, Osaka (IFO), Japan.

Further, in the method of the present invention, *Gluconobacter suboxydans* BL-9 (IFO 14489, FERM BP-1241) and *Gluconobacter suboxydans* BL-115 (IFO 14490, FERM BP-1240) disclosed in our European Patent Application No. 233050 (A2) noted above can be used. These IFO; FERM numbers represent accession numbers at Institute for Fermentation Osaka (IFO) of 17–85, Juso-honmachi 2-chome, Yodogawa-ku, Osaka, Japan; and at Fermentation Research Institute, Agency of Industrial Science and Technology, Ministry of International Trade and Industry, Japan (FRI) of 1–3, Yatabemachi-higashi 1-chome, Tsukuba, Ibaraki, Japan, respectively. Both strains were deposited at IFO on Jan. 21, 1986, at FRI on Feb. 1, 1986 and (converted to deposits under the Budapest Treaty on Dec. 22, 1986).

The term "growth phase" of the above microorganisms used herein means the lag phase and a culturing period until the end of the logarithmic growth phase in culturing of the microorganisms used. The growth phase is varied according to a particular kind of a microorganism used, culturing conditions and the like, but can be readily determined by preparing a growth curve according to a conventional method. Generally, the growth phase is corresponding to the culturing period required for consumption of a nitrogen source in a culture medium, and in many cases, it is corresponding to, for example, about 9 hours after starting culturing.

In the present invention, an initial charge concentration of D-sorbitol is optimized to 8 to 25% to improve the growth rate and, as described in the above (1), the remaining D-sorbitol is continuously or intermittently added in such a concentration that it does not go up to over about 5% during and after the growth phase of the microorganism used to reach a final charge concentration of 40 to 60%.

Figure 2:
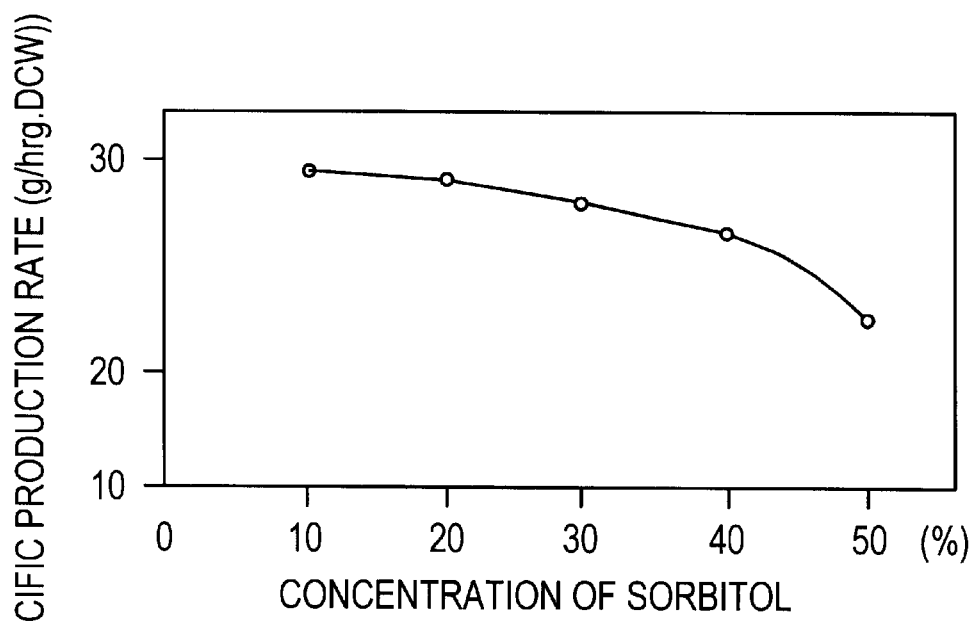
FIG. 2 is a graph illustrating the relationship between a concentration of D-sorbitol and a production rate of L-sorbose.

The initial charge concentration of D-sorbitol is preferably 8 to 25%. That is, the accompanying FIGS. 1 and 2 illustrates the effect of the initial charge concentration of D-sorbitol on a specific growth rate and the effect of the concentration of D-sorbitol on a specific production rate of L-sorbose, respectively. As shown in FIGS. 1 and 2, when the concentration of D-sorbitol is 8 to 25%, particularly, 8 to 20%, the specific growth rate and the specific production rate of L-sorbose are increased.

During and after the growth phase, as described above, the charge concentration of D-sorbitol is kept below about 5% so that oxidation of D-sorbitol into L-sorbose proceeds efficiently. On the contrary, when the charge concentration of D-sorbitol goes up to over 5%, the conversion into L-sorbose is delayed and a culturing time is prolonged because the microorganisms are liable to be inhibited by the substrate.

In a conventional method, culturing is carried out by charging all D-sorbitol at once at the beginning of culturing. Therefore, the microorganisms are strongly inhibited by the substrate and a long culturing time is required. However, when addition of D-sorbitol is carried out as in the present invention, a culturing time is shortened. In this respect, the method of the present invention was compared with a conventional method (charged at once). The results are as shown in Table 1.

TABLE 1

| Concentration of D-sorbitol | Maximum Specific Growth Rate | Maximum Oxidation Rate | Time Required for Fermentation (hr) |
|---|---|---|---|
| 30% (charged at once) | 0.22 (hr$^{-1}$) | 24.2 (g/l · hr) | 19 |
| 35% (charged at once) | 0.17 | 22.7 | 24 |
| 40% (charged at once) | 0.12 | 21.3 | 28 |
| 50% (charged at once) | 0.05 | 15.7 | 47 |
| 50% (the present invention) | 0.28 | 29.1 | 20 |

As seen from Table 1, when a 50% solution of D-sorbitol is charged, the culturing requires 47 hours in the conventional method, whereas it requires only 20 hours in the method of the present invention.

The concentration of D-sorbitol in the above culture medium is controlled by calculating a theoretical amount of oxygen required for oxidation of D-sorbitol into L-sorbose. That is, the amount of D-sorbitol is not determined directly, and a prescribed amount (8–25%) of D-sorbitol is charged in the medium and culturing is carried out by supplying the culture with a theoretical amount of oxygen so that this amount becomes 5% or less. Then, culturing is continued by adjusting addition of D-sorbitol to meet supply of oxygen so that the concentration thereof does not go up to over 5%.

In the present invention, the oxygen demand of the microorganisms can be satisfied only by oxygen from air in the early stage of culturing. However, as described in the above (2), when the microorganism concentration and the oxygen demand of the microorganisms are increased during and after the growth phase, a culture exhaust gas which has been enriched with oxygen gas such as that from liquid oxygen to increase the partial pressure of oxygen (for example, oxygen enriched gas the oxygen partial pressure of which is increased to 21% or higher, preferably, 21 to 50%) is circulated into a culture liquid to supply the insufficiency of oxygen to control the concentration of oxygen dissolved in the culture medium to 0.7 ppm or higher, preferably, 1 to 4 ppm.

The supply of the above oxygen is stoichiometrically determined based on the above D-sorbitol. In culturing of the present invention, even if excess dissolved oxygen which is not utilized in the reaction is present in the culture medium, in principle, it does not effect the production of L-sorbose. However, it is economical to supply a culture tank with oxygen in a proper amount and, in practice, by considering that there may be unevenness of the concentration of dissolved oxygen in a culture tank, the concentration of dissolved oxygen is controlled to 0.7 ppm or higher, preferably, 1 to 4 ppm as described above.

Figure 3:
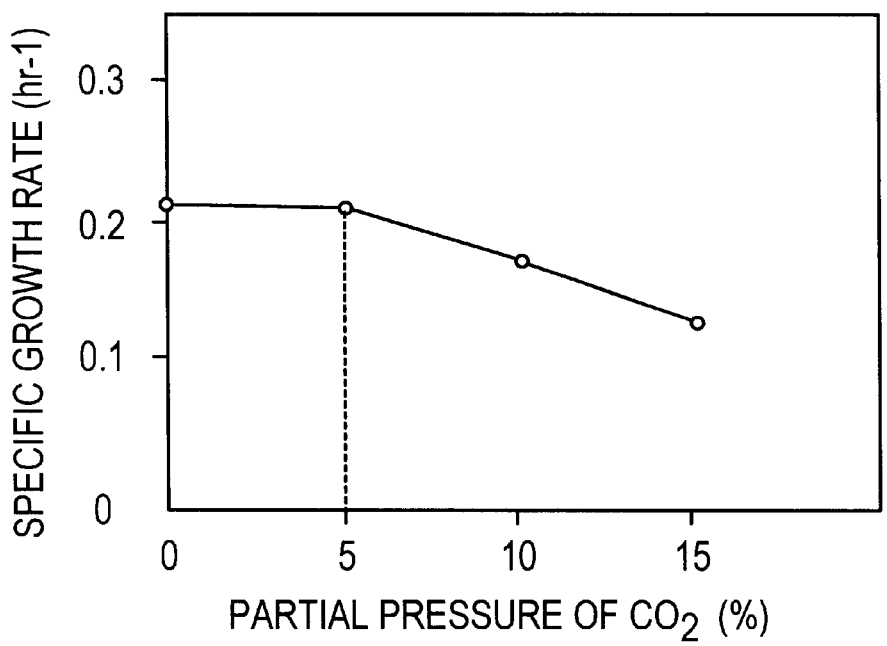
FIG. 3 is a graph illustrating the relationship between a partial pressure of carbon dioxide gas and a specific growth rate.
Figure 4:
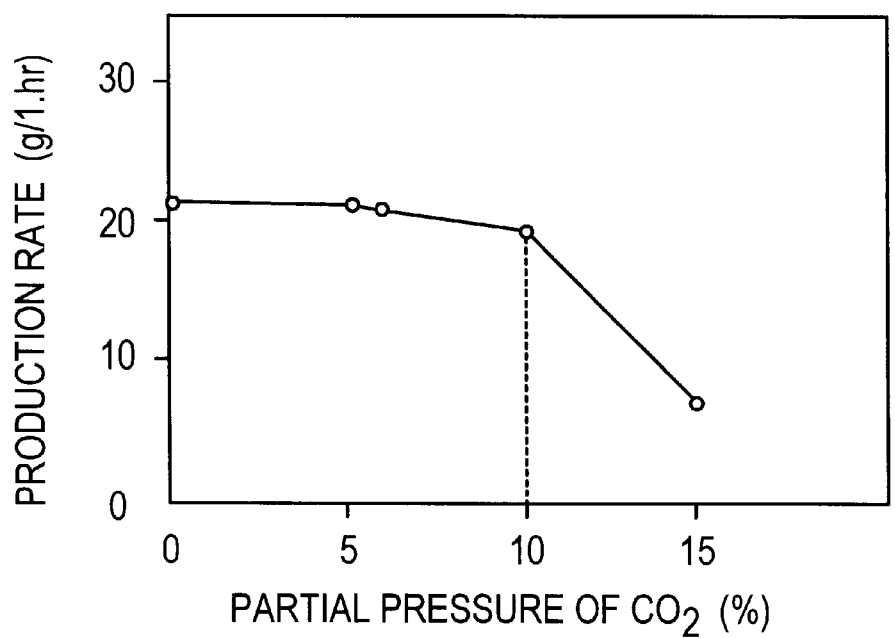
FIG. 4 is a graph illustrating the relationship between a partial pressure of carbon dioxide gas and a production rate of L-sorbose.

In the present invention, culturing is economized by circulating a culture exhaust gas having an increased partial pressure of oxygen as described above into a culture liquid during and after the growth phase of the microorganisms. However, it is known that, when an exhaust gas is reused by circulation, carbon dioxide gas generated by respiration of the microorganisms is accumulated and growth and oxidation activity of the microorganisms are inhibited. That is, the accompanying FIGS. 3 and 4 illustrate the effects of the partial pressure of carbon dioxide gas on the specific growth rate and the production rate of L-sorbose, respectively. As shown in FIGS. 3 and 4, when the concentration of carbon dioxide gas exceeds 5%, the specific growth rate is strongly inhibited. On the other hand, although the production rate (oxidation rate) of L-sorbose is not so strongly inhibited in comparison with the specific growth rate, it is inhibited a little, when the concentration of carbon dioxide gas exceeds 5%, and is strongly inhibited, when the concentration of carbon dioxide gas exceeds 10%. Therefore, in the present invention, a part of the exhaust gas circulated (5–10%) is released to the atmosphere, and oxygen gas is supplied in such an amount that it meets the released amount of oxygen plus oxygen consumed by the microorganisms to dilute the concentration of carbon dioxide gas. Thereby, the partial pressure of carbon dioxide gas in the circulating gas is controlled to 10% or lower which does not adversely affect the production rate. According to the present invention, as described above, an adsorbent which is used in a convention method is not required. This is advantageous from the viewpoints of maintenance and economy. Further, even if this release to the atmosphere is employed, 60% of the amount of oxygen to be used can be reduced by reusing the exhaust gas having the increased partial pressure of oxygen, which results in a great economical advantage.

Furthermore, in the method of the present invention, a culture medium having definite components, such as a synthetic medium or a semisynthetic medium, is used as a production medium. Thereby, the medium is stabilized and the raw material cost is economized. That is, in the method of the present invention, as the carbon sources, D-sorbitol is used as the main raw material, and in addition, there can be added D-glucose, D-fructose, D-mannitol, ethanol, molasses, starch, starch hydrolysates and the like. And, as the nitrogen sources, there can be used organic nitrogen-containing compounds such as amino acids, urea and the like, in addition to inorganic nitrogen-containing compounds such as ammonium sulfate, ammonium nitrate, ammonium acetate, aqueous ammonium chloride solution, ammonium phosphate, aqueous ammonium solution, ammonia gas and the like. Furthermore, in addition to the above carbon and nitrogen sources, there can be added various metals, vitamins, amino acids, nucleic acids, quinones and the like, which are necessary for the growth of the microorganisms used, to the culture medium.

Particularly, in the present invention, 0.04 to 0.07% of one or more glycogenic amino acids have been added to the culture medium as a component to enhance the oxidation activity of the microorganisms. The relationship between a viable cell number and a rate of oxidation in the case that various amino acids have been added to the medium, as well as time required for completion of fermentation in the case that the culturing is carried out by adding these amino acids and charging a 50% solution of D-sorbitol are shown in Table 2.

TABLE 2

| | Viable Cell Number ($\times 10^8$/ml) | | Rate of Oxidation | Time Required for Fermentation of 50% solution |
|---|---|---|---|---|
| | Max. | Min. | (g/l · hr) | (hr) |
| Glycine | 0.78 | 0.78 | 6.9 | 33 |
| Serine | 3.2 | 3.2 | 19.8 | 19.5 |
| Threonine | 2.6 | 2.6 | 17.6 | 20.5 |

TABLE 2-continued

| | Viable Cell Number (× 10⁸/ml) | | Rate of Oxidation | Time Required for Fermentation of 50% solution |
|---|---|---|---|---|
| | Max. | Min. | (g/l · hr) | (hr) |
| Alanine | 4.5 | 4.5 | 20.3 | 18.5 |
| Valine | 4.2 | 1.7 | 13.7 | 28 |
| Leucine | 4.9 | 0.77 | 12.6 | 29 |
| Isoleucine | 1.9 | 1.1 | 15.2 | 26 |
| Cystine | 3.5 | 0.54 | 11.7 | 31 |
| Methionine | 3.9 | 3.9 | 17.5 | 22 |
| Tryptophan | 3.4 | 1.9 | 16.5 | 24 |
| Phenylalanine | 3.2 | 0.85 | 14.0 | 27 |
| Tyrosine | 0.4 | 0.19 | 8.2 | 32 |
| Proline | 3.1 | 1.5 | 16.6 | 24 |
| Aspartic acid | 4.0 | 4.0 | 18.0 | 20.5 |
| Glutamic acid | 4.4 | 4.4 | 21.3 | 18 |
| Lysine | 3.5 | 1.8 | 15.1 | 25 |
| Histidine | 1.5 | 0.26 | 10.5 | 28.5 |
| Arginine | 3.3 | 2.2 | 11.4 | 30 |
| Asparagine | 3.5 | 3.14 | 18.3 | 20 |
| Glutamine | 4.6 | 3.9 | 20.9 | 18.5 |
| Ammonium acetate | 3.4 | 1.0 | 17.7 | 21 |
| No addition | 0.93 | 0.77 | 4.4 | 35 |

Note: All amino acids are L-forms.

As shown in Table 2, the viable cell number can be increased without lowering the rate of oxidation per the viable cell number by adding glycogen amino acids such as glutamic acid, glutamine, alanine, serine, threonine, asparagine, aspartic acid and the like. Further, it is recognized that, when culturing of 50% solution is carried out by adding these amino acids, the time required for completion of fermentation can be shortened.

In the present invention, culturing conditions other than those described above are not specifically limited. That is, culturing temperature is generally 15° C. to 45° C., more preferably, 25° C. to 40° C. The pH of the culture medium is generally 3.0 to 8.0, more preferably, 3.5 to 6.5. Culturing time is generally 10 to 100 hours, more preferably, 15 to 40 hours.

Further, the present invention provides an apparatus for culturing microorganisms which is suitable for carrying out the method for producing L-sorbose as described above.

That is, the present invention provides an apparatus for culturing a microorganism which comprises, a culture tank for culturing the microorganism equipped with a stirrer, a gas inlet provided at the lower part of the tank and an exhaust vent provided at the upper part of the tank;

a substrate feeding device for adding a culture substrate (D-sorbitol) to said culture tank;

an oxygen supply device comprising a liquid oxygen storage tank and an evaporator for supplying said culture tank with a culture exhaust gas which has been enriched with oxygen gas;

a dissolved oxygen concentration detector for detecting dissolved oxygen of a culture liquid in said culture tank to output a signal of the concentration of dissolved oxygen;

a dissolved oxygen controller for controlling supply of dissolved oxygen by detecting said signal of the concentration of dissolved oxygen;

a carbon dioxide gas measuring device for measuring a partial pressure of carbon dioxide gas in a culture exhaust gas, which is provided to an exhaust gas pipe from said culture tank;

an exhaust gas release device for releasing a part of the culture exhaust gas out of the system by detecting said partial pressure of carbon dioxide gas;

a conduit for circulating the remainder of said culture exhaust gas to the gas inlet of the culture tank; and an air supply device for supplying said culture tank with air.

In the culturing apparatus of the present invention, a dissolved oxygen sensor composed of Galvani's oxygen electrode, etc. is used as the dissolved oxygen concentration detector in a culture liquid of a culture tank, and the divergence of an air flow valve or an oxygen gas control valve is controlled according to the signal of the concentration of dissolved oxygen through the dissolved oxygen controller which receives the detection signal from the dissolved oxygen sensor. Thereby, the concentration of dissolved oxygen in a culture liquid is controlled to proper conditions, that is, to 0.7 ppm or higher, preferably, 1 to 4 ppm.

Further, feed of the culture substrate (D-sorbitol) to the culture tank is carried out by adding it continuously or intermittently according to a supply rate of oxygen to the culture tank during and after the growth phase of the microorganism with preventing that the concentration of D-sorbitol in the culture liquid goes up to over 5% so that a high concentration of D-sorbitol is oxidized to L-sorbose within a short period of time.

Further, the apparatus of the present invention economizes resources by recovering the exhaust gas having increased partial pressure of oxygen with a compressor to circulate and reuse. In order to optimize the partial pressure of carbon dioxide gas in the circulating exhaust gas, an apparatus for measuring the partial pressure of carbon dioxide gas such as an infrared absorption analyzer or the like is provided at the pathway of the exhaust gas. According to the partial pressure of carbon dioxide gas measured by the measuring apparatus, the proper amount of exhaust gas is released by controlling the divergence of an air release valve provided at the pathway and thereby the partial pressure of carbon dioxide gas in the exhaust gas returned to the culture tank is controlled to a proper value (10% or less). Thus, in the present invention, the apparatus and maintenance are simplified by employing release of a part of the exhaust gas into the atmosphere instead of an adsorbent used in a conventional apparatus for removal of carbon dioxide gas.

Furthermore, in the apparatus of the present invention, the partial pressure of oxygen gas in the exhaust gas is measured by means of a measuring apparatus of the partial pressure of oxygen gas composed of Zirconia's analyzer, etc., while the partial pressure of oxygen at the inlet to the culture tank is calculated from both circulating flow rate and fresh air aeration rate, to determine oxygen consumption. Then, the amount of the substrate to be oxidized is estimated from the oxygen consumption.

Figure 5:
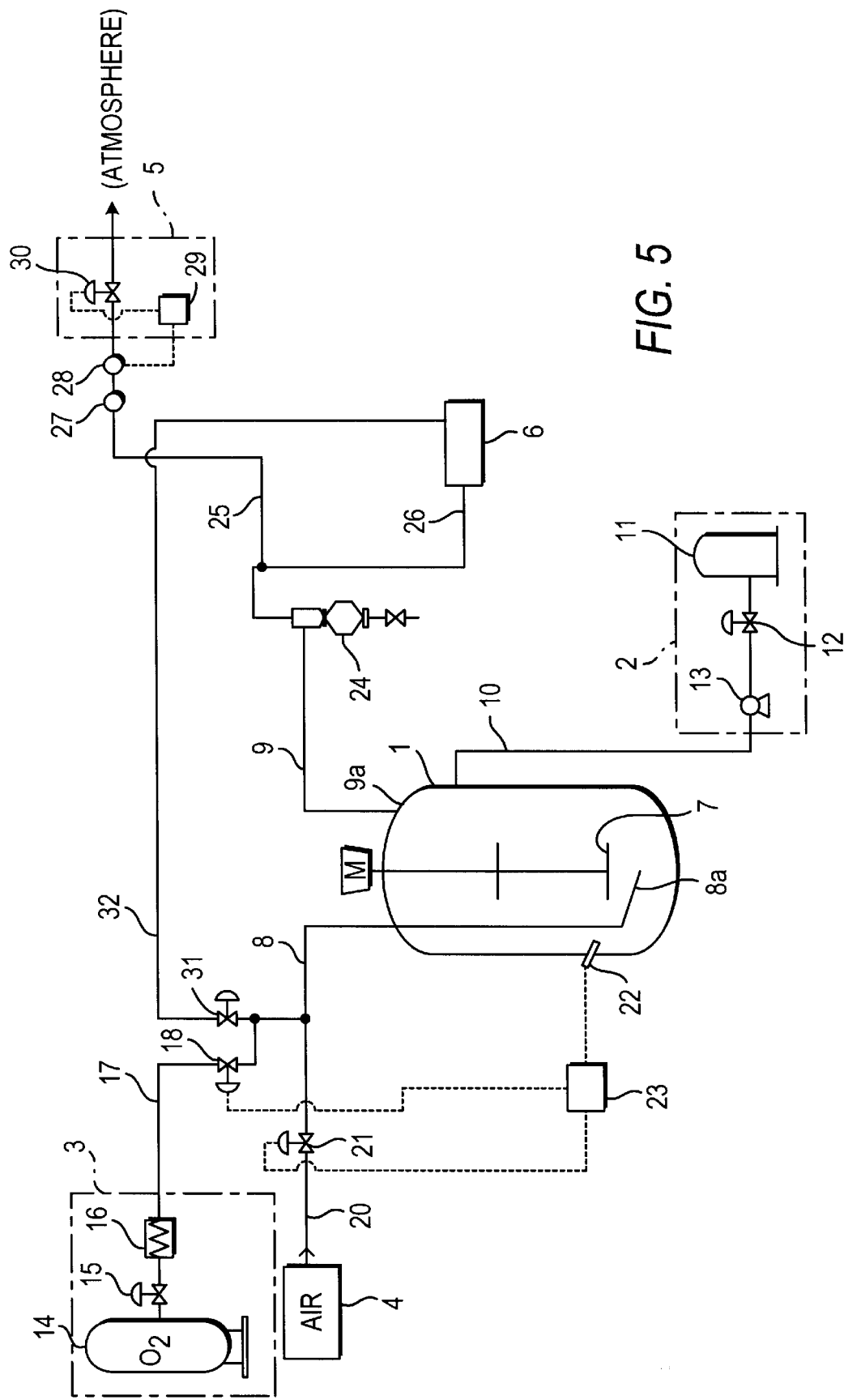
FIG. 5 is a general view of a preferred example of a culturing apparatus of the present invention.

Now, a preferred embodiment of the apparatus of the present invention is illustrated by using the accompanying FIG. 5.

FIG. 5 shows a general view of a preferred example of a culturing apparatus of the present invention.

The apparatus of FIG. 5 comprises a tank 1 for culturing a microorganism, a substrate feeding device 2 for adding a culture substrate (D-sorbitol) to the culture tank 1, an oxygen supply device 3 for supplying oxygen mixed with a culture exhaust gas, an air supply device 4 for supplying the culture tank 1 with air, a gas release device 5 for releasing a part of the exhaust gas from the culture tank 1 into the system, and a compressor 6 for circulating the exhaust gas to the culture tank 1.

Inside the above culture tank 1, there is a stirrer 7 which is driven with a motor. The inlet 8a of a gas supply pipe 8 is connected to the lower part of the tank and the exhaust vent 9a of a gas exhaust pipe 9 is connected to the upper part. A substrate feeding device 2 is also connected to the upper part of the tank via a conduit 10.

The substrate feeding device 2 comprises a substrate tank 11, a substrate feeding valve 12 and a substrate feeding pump 13 so that a culture substrate (D-sorbitol) is fed from the substrate tank 11 to the culture tank 1 through the substrate feed valve 12, the substrate feed pump 13 and the conduit 10. Feed of D-sorbitol is carried out by adding it continuously or intermittently with preventing that the concentration of D-sorbitol in the culture liquid does not go up to over about 5% during and after the growth period of the microorganism in the culture tank 1.

The above gas inlet 8 is connected to the oxygen supply device 3 comprising a liquid oxygen storage tank 14, an emergency shut-off valve 15 and an evaporator 16 through a conduit 17, and oxygen gas formed by vaporizing liquid oxygen with the evaporator 16 is supplied to the culture tank 1 with controlling the supply through an oxygen gas control valve 18 provided at the conduit 17. In the same manner, the gas supply pipe 8 is connected to the air supply device 4 through a conduit 20 and air is supplied to the culture tank 1 through an air flow control valve 21 provided at the conduit 20.

The oxygen gas control valve 18 and the flow control valve 21, which control the supply of oxygen gas and air, are controlled by a dissolved oxygen controller 23 which receives a detection signal from a dissolved oxygen detector 22 installed in the culture tank 1. The dissolved oxygen detector is composed of, for example, Galvani's oxygen electrode. It detects the concentration of dissolved oxygen of the culture liquid in the culture tank to output a signal of the concentration of dissolved oxygen to the dissolved oxygen controller 23, and the divergences of the oxygen gas control valve 18 and the flow control valve 21 are controlled by the dissolved oxygen controller 23 which has detected the signal.

Air is supplied from the air supply device 4 to the culture tank 1 so that the concentration of dissolved oxygen becomes a constant level until the growth phase of the microorganism. During and after the growth phase of the microorganism, the supply of air is stopped and oxygen gas is supplied from the oxygen supply device 3 to the culture tank 1 to control the concentration of dissolved oxygen to 0.7 ppm or higher, preferably, 1 to 4 ppm.

The above exhaust vent 9 is connected to the gas release device via a mist separator 24 and a conduit 25, and is also connected to the compressor 6 via a conduit 26. A measuring apparatus for the partial pressure of oxygen 27 composed of Zirconia's analyzer, etc. and a measuring apparatus for the partial pressure of carbon dioxide gas such as an infrared absorption analyzer, etc. are provided to the conduit 25. The partial pressure of carbon dioxide gas in the exhaust gas is detected by the measuring apparatus for the partial pressure of carbon dioxide gas 28 and a signal of the detector is output to a carbon dioxide gas partial pressure controller 29. A divergence of a air release valve 30 of the gas release device 5 is controlled by the controller 29 to release a part of the culture exhaust gas out of the system.

On the other hand, the compressor 6 is connected to the gas supply pipe 8 via a conduit for circulation 32 provided to an aeration circulating valve 31. The remainder of the exhaust gas which is not released from the gas release device 5 is circulated by the compressor 6 to return it to the culture tank 1 via the gas supply pipe 8 with controlling the flow rate by the aeration circulating valve 31. This exhaust gas are circulated and reused together with supply of pure oxygen gas during and after the growth phase of the microorganism. Thereby, the oxygen enriched gas which is a mixture of oxygen gas and the exhaust gas is circulated to the culture tank 1.

The working of the above apparatus is illustrated in turn hereinafter.

(a) Air is supplied from the air supply device 4 to the culture tank 1 with controlling the divergence of the flow control valve 21 by the dissolved oxygen controller 23 so that the concentration of dissolved oxygen of the culture liquid in the culture tank 1 becomes a prescribed constant level. At that time, for example, when the initial charge concentration of the substrate is 20%, air is supplied in the culture tank 1 so that the concentration of dissolved oxygen becomes 2 ppm.

(b) Feed of the substrate from the substrate tank 11 to the culture tank 1 is started at the time when the oxygen consumption corresponding to 15% oxidation of the substrate concentration is calculated by the apparatus for measuring the partial pressure of oxygen 27.

(c) When the flow rate of air from the air supply device 4 to the culture tank 1 reaches a maximum and the dissolved oxygen concentration can not be maintained at the prescribed level, the oxygen gas control valve 18 is opened by the dissolved oxygen controller 23 to supply the culture tank 1 with oxygen gas.

(d) Immediately after the control of the concentration of dissolved oxygen by oxygen gas is started, the aeration circulating valve 31 is opened and the compressor 6 is started to circulate the exhaust gas to the culture tank 1, and the flow control valve 21 is closed. Thereafter, the concentration of dissolved oxygen is maintained only by oxygen gas.

(e) When the circulation of the exhaust gas is started, carbon dioxide gas is accumulated in the aerated gas. Accordingly, the partial pressure of carbon dioxide gas in the exhaust gas is measured by the measuring apparatus 28 and then the air release valve 30 is opened by the controller for the partial pressure of carbon dioxide gas 29 to release a part of the exhaust gas into the atmosphere and to maintain the partial pressure of carbon dioxide gas in the aerated gas below a constant value (10%).

(f) When the prescribed amount of substrate is fed into the culture tank 1, the feed is stopped.

(g) When the fermentation proceeds in the culture tank 1 and reached toward the end, the required amount of oxygen is decreased. Accordingly, the inflow of oxygen into the culture tank 1 is stopped and the compressor is stopped. Further, the inflow of the exhaust gas into the culture tank 1 is stopped by closing the aeration circulating valve 31 and air supply from the air supply device 4 is reopened.

(h) The concentration of dissolved oxygen in the culture tank 1 rises rapidly by the above aeration and the partial pressure of oxygen also rises. The fermentation is completed when the partial pressure of oxygen in the exhaust gas reaches a prescribed value (20%).

The following Examples illustrate the process of the present invention in detail but are not to be construed to limit the scope thereof. In the following Examples, the apparatus as shown in FIG. 5 was used.

EXAMPLE 1

*Gluconobacter suboxydans* IFO 3254 was inoculated in 10 liters of a culture medium containing 20% of D-sorbitol, 0.2% of sodium glutamate, 0.018% of calcium carbonate, 0.003% of nicotinamide, 0.003% of calcium pantothenate, 0.0001% of vitamin $B_2$, 0.0001% of p-aminobenzoic acid, 0.047% of potassium dihydrogen phosphate, 0.03% of yeast extract, 0.01% of magnesium sulfate, 0.00015% of ferrous sulfate, 0.00001% of manganese sulfate and 0.0005% of actocol and incubated at 30° C. for 24 hours. As a seed, this was transferred to 49 liters of a culture medium containing 20% of D-sorbitol, 0.06% of ammonium acetate, 0.102% of sodium glutamate, 0.06% of calcium carbonate, 0.006% of nicotinamide, 0.0005% of calcium pantothenate, 0.0002% of vitamin $B_2$, 0.00002% of p-aminobenzoic acid, 0.04% of potassium dihydrogen phosphate, 0.02% of magnesium sulfate, 0.0003% of ferrous sulfate and 0.00002% of manganese sulfate.

This was incubated at 30° C. and, after starting culturing, the amount of aeration from the air supply device 4 and the internal pressure of the culture tank were controlled in the range of 0.1 to 0.6 vvm and 0.1 to 1.8 kg/cm$^2$G, respectively so that the concentration of dissolved oxygen was maintained within the range of 2.5±0.5 ppm. After the maximum amount of aeration and the internal pressure reached 0.6 vvm and 1.8 kg/cm$^2$G, respectively, oxygen gas formed by vaporizing liquid oxygen in the oxygen supply device 3 was introduced into the gas inlet 8 and then bubbled through the culture tank 1 so that the concentration of dissolved oxygen became 2.5±0.5 ppm. At the same time, aeration was stopped and the compressor 6 was started to recover the exhaust gas. The exhaust gas was circulated to the culture tank 1. Thereafter, a part of circulating air (0.03 vvm) was released to the atmosphere by the exhaust gas release device 5 to prevent the accumulation of carbon dioxide gas. The concentration of dissolved oxygen was maintained by bubbling oxygen gas. The amount of air being insufficient to maintain the internal pressure was supplied by air from dwell.

On the other hand, addition of D-sorbitol which was oxidized with progress of culturing was started through the substrate feeder 2 to the culture tank 1 at the time when the concentration thereof in the culture liquid became 5%, and the culturing was carried out with addition of 51 liters of a 60 w/w % aqueous D-sorbitol solution for 20 hours in all.

According to the above culturing, it made possible to carry out the culturing with 50 w/v % of D-sorbitol charge concentration per batch in 20 hours, and L-sorbose was accumulated in the yield of 95% based on D-sorbitol.

EXAMPLE 2

*Gluconobacter suboxydans* IFO 3254 was inoculated into 10 liters of a culture medium containing 20% of D-sorbitol, 0.2% of sodium glutamate, 0.018% of calcium carbonate, 0.003% of nicotinamide, 0.003% of calcium pantothenate, 0.0001% of vitamin $B_2$, 0.0001% of p-aminobenzoic acid, 0.047% of potassium dihydrogen phosphate, 0.03% of yeast extract, 0.01% of magnesium sulfate, 0.00015% of ferrous sulfate, 0.00001% of manganese sulfate and 0.0005% of actocol and incubated at 30° C. for 24 hours. As a seed, this was transferred to 54 liters of a culture medium containing 25% of D-sorbitol, 0.08% ammonium acetate, 0.067% of alanine, 0.06% of calcium carbonate, 0.006% of nicotinamide, 0.0005% of calcium pantothenate, 0.0002% of vitamin $B_2$, 0.00002% of p-aminobenzoic acid, 0.04% of potassium dihydrogen phosphate, 0.02% of magnesium sulfate, 0.0003% of ferrous sulfate and 0.00002% of manganese sulfate.

This was incubated at 30° C. and after starting culturing, the amount of aeration from the air supply device 4 and the internal pressure of the culture tank were controlled in the range of 0.1 to 0.6 vvm and 0.1 to 1.8 kg/cm$^2$G, respectively, so that the concentration of dissolved oxygen became 2.5±0.5 ppm. After the maximum amount of aeration and the internal pressure reached 0.6 vvm and 1.8 kg/ch$^2$G, respectively, oxygen gas formed by vaporizing liquid oxygen in the oxygen supply device 3 was introduced into the gas inlet 8 and then bubbled through the culture tank 1 so that the concentration of dissolved oxygen reached 2.5±0.5 ppm. At the same time, aeration was stopped and the compressor 6 was started to recover the exhaust gas. The exhaust gas was circulated to the culture tank 1. Thereafter, a part of circulating air (0.03 vvm) was released to the atmosphere by the exhaust gas release device 5 to prevent the accumulation of carbon dioxide gas. The concentration of dissolved oxygen was maintained by bubbling oxygen gas. The amount of air being insufficient to maintain the internal pressure was supplied by air from dwell.

On the other hand, addition of D-sorbitol oxidized with progress of culturing was started through the substrate feeder 2 to the culture tank 1 at the time when the concentration thereof in the culture liquid became 5%, and culturing was carried out with addition of 51 liters of a 60 w/w % aqueous D-sorbitol solution for 20 hours in all.

According to the above culturing, it made possible to carry out the culturing with 50 w/v % of D-sorbitol concentration charged per batch in 20 hours, and L-sorbose was accumulated in the yield of 95% based on D-sorbitol.

EXAMPLE 3

*Gluconobacter suboxydans* BL-9 (IFO 14489, FERM BP-1241) was inoculated in 10 liters of a culture medium containing 20% of D-sorbitol, 0.3% of glycerin, 0.2% of sodium glutamate, 0.018% of calcium carbonate, 0.003% of nicotinamide, 0.003% of calcium pantothenate, 0.0001% of vitamin $B_2$, 0.0001% of p-aminobenzoic acid, 0.047% of potassium dihydrogen phosphate, 0.01% of magnesium sulfate, 0.00015% of ferrous sulfate, 0.00001% of manganese sulfate and 0.0005% of actocol and incubated at 30° C. for 24 hours. As a seed, this was transferred to 49 liters of a culture medium containing 20% of D-sorbitol, 0.05% of glutamic acid, 0.06% of ammonium acetate, 0.102% of sodium glutamate, 0.06% of calcium carbonate, 0.006% of nicotinamide, 0.0005% of calcium pantothenate, 0.0002% of vitamin $B_2$, 0.00002% of p-aminobenzoic acid, 0.04% of potassium dihydrogen phosphate, 0.02% of magnesium sulfate, 0.0003% of ferrous sulfate and 0.00002% of manganese sulfate.

This was incubated at 30° C. and, after starting culturing, the amount of aeration from the air supply device 4 and the internal pressure of the culture tank were controlled in the range of 0.1 to 0.6 vvm and 0.1 to 1.8 kg/cm$^2$G, respectively so that the concentration of dissolved oxygen was maintained within the range of 2.5±0.5 ppm. After the maximum amount of aeration and the internal pressure reached 0.6 vvm and 1.8 kg/cm$^2$G, respectively, oxygen gas formed by vaporizing liquid oxygen in the oxygen supply device 3 was introduced into the gas inlet 8 and then bubbled through the culture tank 1 so that the concentration of dissolved oxygen became 2.5±0.5 ppm. At the same time, aeration was stopped and the compressor 6 was started to recover the exhaust gas. The exhaust gas was circulated to the culture tank 1. Thereafter, a part of circulating air (0.03 vvm) was released to the atmosphere by the exhaust gas release device 5 to prevent the accumulation of carbon dioxide gas. The concentration of dissolved oxygen was maintained by bubbling oxygen gas. The amount of air being insufficient to maintain the internal pressure was supplied by air from dwell.

On the other hand, addition of D-sorbitol which was oxidized with progress of culturing was started through the substrate feeder 2 to the culture tank 1 at the time when the concentration thereof in the culture liquid became 5%, and the culturing was carried out with addition of 51 liters of a 60 w/w % aqueous D-sorbitol solution for 20 hours in all.

According to the above culturing, it made possible to carry out the culturing with 50 w/v % of D-sorbitol charge concentration per batch in 20 hours, and L-sorbose was accumulated in the yield of 97.5% based on D-sorbitol.

EXAMPLE 4

*Gluconobacter suboxydans* BL-115 (IFO 14490, FERM BP-1240) was inoculated into 10 liters of a culture medium containing 20% of D-sorbitol, 0.3% of glycerin, 0.2% of sodium glutamate, 0.018% of calcium carbonate, 0.003% of nicotinamide, 0.003% of calcium pantothenate, 0.0001% of vitamin $B_2$, 0.0001% of p-aminobenzoic acid, 0.047% of potassium dihydrogen phosphate, 0.01% of magnesium sulfate, 0.00015% of ferrous sulfate, 0.00001% of manganese sulfate and 0.0005% of actocol and incubated at 30° C. for 24 hours. As a seed, this was transferred to 54 liters of a culture medium containing 25% of D-sorbitol, 0.05% of glycerin, 0.08% ammonium acetate, 0.067% of alanine, 0.06% of calcium carbonate, 0.006% of nicotinamide, 0.0005% of calcium pantothenate, 0.0002% of vitamin $B_2$, 0.00002% of p-aminobenzoic acid, 0.04% of potassium dihydrogen phosphate, 0.02% of magnesium sulfate, 0.0003% of ferrous sulfate and 0.00002% of manganese sulfate.

This was incubated at 30° C. and after starting culturing, the amount of aeration from the air supply device 4 and the internal pressure of the culture tank were controlled in the range of 0.1 to 0.6 vvm and 0.1 to 1.8 kg/cm$^2$G, respectively, so that the concentration of dissolved oxygen became 2.5±0.5 ppm. After the maximum amount of aeration and the internal pressure reached 0.6 vvm and 1.8 kg/ch$^2$G, respectively, oxygen gas formed by vaporizing liquid oxygen in the oxygen supply device 3 was introduced into the gas inlet 8 and then bubbled through the culture tank 1 so that the concentration of dissolved oxygen reached 2.5±0.5 ppm. At the same time, aeration was stopped and the compressor 6 was started to recover the exhaust gas. The exhaust gas was circulated to the culture tank 1. Thereafter, a part of circulating air (0.03 vvm) was released to the atmosphere by the exhaust gas release device 5 to prevent the accumulation of carbon dioxide gas. The concentration of dissolved oxygen was maintained by bubbling oxygen gas. The amount of air being insufficient to maintain the internal pressure was supplied by air from dwell.

On the other hand, addition of D-sorbitol oxidized with progress of culturing was started through the substrate feeder 2 to the culture tank 1 at the time when the concentration thereof in the culture liquid became 5%, and culturing was carried out with addition of 51 liters of a 60 w/w % aqueous D-sorbitol solution for 20 hours in all.

According to the above culturing, it made possible to carry out the culturing with 50 w/v % of D-sorbitol concentration charged per batch in 20 hours, and L-sorbose was accumulated in the yield of 97.3% based on D-sorbitol.

What is claimed is:

1. An industrial production method for producing L-sorbose by microbial oxidation of D-sorbitol using a microorganism of the genus Gluconobacter, comprising:

a) providing a culture medium having definite components for culturing the microorganism of the genus Gluconobacter which includes at least one amino acid selected from the group consisting of glutamic acid, glutamine, alanine, serine, threonine, asparagine and aspartic acid;

b) adding D-sorbitol to the culture medium in an amount such that the concentration of D-sorbitol is maintained at or under 5% by weight of the culture medium during and after the growth phase of the microorganism;

c) pumping oxygen gas into the culture medium and monitoring the amount of dissolved oxygen in the culture medium such that the concentration of the dissolved oxygen in the culture medium is maintained in a prescribed range, the culture medium releasing an exhaust gas comprising oxygen and carbon dioxide;

d) nonadsorbently controlling the partial pressure of carbon dioxide in the culture tank by venting via a valve a portion of the exhaust gas from the culture tank, the partial pressure of carbon dioxide in the culture tank being maintained in the range from 5 to 10% by such venting; and e) releasing to the atmosphere some of the exhaust gas which has been vented from the culture tank and recirculating the remaining exhaust gas which has been vented but not released back to the culture medium by mixing such exhaust gas, which includes carbon dioxide produced by the culture medium, with the oxygen gas prior to the oxygen gas being pumped into the culture medium, whereby L-sorbose is efficiently produced by the microbial oxidation of D-sorbitol.

2. The method of claim 1, wherein the culture medium includes an initial charge concentration of D-sorbitol prior to the growth phase of the microorganism, the initial charge concentration being in the range of 8 to 25% by weight of the culture medium.

3. The method of claim 1, wherein the culture medium includes an initial charge concentration of D-sorbitol prior to the growth phase of the microorganism, the culture medium processing a total amount of D-sorbitol prior to, during and after the growth phase of the microorganism, the total amount being in the range of 40 to 60% by weight of the culture medium.

4. The method of claim 1, wherein the concentration of the dissolved oxygen in the culture medium is maintained in the range of 1 to 4 ppm.

5. The method of claim 1, wherein the amino acid concentration in the culture medium is in the range of 0.04 to 0.07% by weight.

6. The method of claims 1, wherein the temperature of the culture medium is maintained between 25° C. and 40° C.

7. The method of claim 1, wherein the pH of the culture medium is maintained between 3.5 and 6.5.

8. An industrial production method for producing L-sorbose by microbial oxidation of D-sorbitol using a microorganism of the genus gluconobacter, comprising:

a) providing a culture medium having definite components for culturing the microorganism of the genus Gluconobacter which includes at least one amino acid selected from the group consisting of glutamic acid, glutamine, alanine, serine, threonine, asparagine and aspartic acid, the culture medium being disposed in a culture tank;

b) adding D-sorbitol to the culture medium in an amount such that the concentration of D-sorbitol is maintained at or under 5% by weight of the culture medium during and after the growth phase of the microorganism;

c) pumping oxygen gas into the culture medium and monitoring the amount of dissolved oxygen in the culture medium such that the concentration of the dissolved oxygen in the culture medium is maintained in a prescribed range, the culture medium releasing an exhaust gas comprising oxygen and carbon dioxide;

d) nonadsorbently controlling the partial pressure of carbon dioxide in the culture tank by venting via a valve a portion of the exhaust gas from the culture tank, the partial pressure of carbon dioxide in the culture tank being maintained in a prescribed range by such venting; and e) releasing to the atmosphere some of the exhaust gas which has been vented from the culture tank and recirculating the remaining exhaust gas which has been vented but not released back to the culture medium by mixing such exhaust gas, which includes carbon dioxide produced by the culture medium, with the oxygen gas prior to the oxygen gas being pumped into the culture medium, whereby L-sorbose is efficiently produced by the microbial oxidation of D-sorbitol.

9. An industrial production method for producing L-sorbose by microbial oxidation of D-sorbitol using a microorganism of the genus Gluconobacter, comprising:

a) providing a culture medium having definite components for culturing the microorganism of the genus Gluconobacter which includes at least one amino acid selected from the group consisting of glutamic acid, glutamine, alanine, serine, threonine, asparagine and aspartic acid;

b) adding D-sorbitol to the culture medium in an amount such that the concentration of D-sorbitol does not substantially inhibit the production of L-sorbose in the culture medium during and after the growth phase of the microorganism;

c) pumping oxygen gas into the culture medium and monitoring the amount of dissolved oxygen in the culture medium such that the concentration of the dissolved oxygen in the culture medium is maintained in a prescribed range, the culture medium releasing an exhaust gas comprising oxygen and carbon dioxide;

d) nonadsorbently controlling the partial pressure of carbon dioxide in the culture tank by venting via a valve a portion of the exhaust gas from the culture tank, the partial pressure of carbon dioxide in the culture tank being maintained in the range from 5 to 10% by such venting; and e) releasing to the atmosphere some of the exhaust gas which has been vented from the culture tank and recirculating the remaining exhaust gas which has been vented but not released back to the culture medium by mixing such exhaust gas, which includes carbon dioxide produced by the culture medium, with the oxygen gas prior to the oxygen gas being pumped into the culture medium, whereby L-sorbose is efficiently produced by the microbial oxidation of D-sorbitol.

10. A method for recycling exhaust gas produced by a microbiological industrial process in a culture tank, comprising:

a) carrying out the microbiological process in a culture medium in the culture tank, the exhaust gas produced by the microbiological process comprising carbon dioxide; then b) venting some of the exhaust gas from the culture tank to maintain the partial pressure of the carbon dioxide in the culture tank within a prescribed range; and then c) releasing to the atmosphere some of the exhaust gas which has been vented and recycling the remainder of exhaust gas, which has been vented but not released and which includes carbon dioxide, back into the culture medium in the culture tank without adsorbing carbon dioxide from such exhaust, gas whereby the microbiological process is cost efficient.

11. A recycling process which comprises:

recycling an exhaust gas, which includes carbon dioxide and which is produced by a microbiological process carried out in a culture medium, back into the culture medium without adsorbing carbon dioxide from the exhaust gas and enriching with oxygen the exhaust gas which is recycled back into the culture medium.

12. An industrial production method for producing L-sorbose by microbial oxidation of D-sorbitol using a microorganism of the genus Gluconobacter, comprising:

a) providing a culture medium for culturing the microorganism of the genus Gluconobacter which includes at least one amino acid selected from the group consisting of glutamic acid, glutamine, alanine, serine, threonine, asparagine and aspartic acid, the concentration of the amino acid in the culture medium being 0.04 to 0.07% by weight, the culture medium being a nonliving culture medium exclusive of the microorganism such that the culture medium is stable and its ingredients definitive, the temperature of the culture medium being maintained between 25° C. and 40° C., the pH of the culture medium being maintained between 3.5 and 6.5, the culture medium including an initial charge concentration of D-sorbitol prior to the growth phase of the microorganism, the initial charge concentration being in the range of 8 to 25% by weight of the culture medium;

b) adding D-sorbitol to the culture medium in an amount such that the concentration of D-sorbitol is maintained at or under 5% by weight of the culture medium during and after the growth phase of the microorganism, the culture medium processing a total amount of D-sorbitol prior to, during and after the growth phase of the microorganism, in the range of 40 to 60% by weight of the culture medium;

c) pumping oxygen gas into the culture medium and monitoring the amount of dissolved oxygen in the culture medium such that the concentration of the dissolved oxygen in the culture medium is maintained in the range of 1 to 4 ppm, the culture medium releasing an exhaust gas comprising oxygen and carbon dioxide;

d) nonadsorbently controlling the partial pressure of carbon dioxide in the culture tank by venting via a valve a portion of the exhaust gas from the culture tank, the partial pressure of carbon dioxide in the culture tank being maintained in the range from 5 to 10% by such venting; and e) releasing to the atmosphere some of the exhaust gas which has been vented from the culture tank and recirculating the remaining exhaust gas which has been vented but not released back to the culture medium by mixing such exhaust gas, which incudes carbon dioxide produced by the culture medium, with the oxygen gas prior to the oxygen gas being pumped into the culture medium, whereby L-sorbose is efficiently produced by the microbial oxidation of D-sorbitol.

* * * * *